United States Patent [19]

Bargar et al.

[11] Patent Number: 4,743,617

[45] Date of Patent: May 10, 1988

[54] HETEROCYCLYL-2-PROPYN-1-AMINES

[75] Inventors: Thomas M. Bargar, Zionsville; Lawrence C. Creemer, Indianapolis, both of Ind.; James R. McCarthy, Cincinnati, Ohio

[73] Assignee: Merrell Dow Pharmaceuticals Inc., Cincinnati, Ohio

[21] Appl. No.: 91,338

[22] Filed: Aug. 31, 1987

Related U.S. Application Data

[63] Continuation of Ser. No. 19,103, Feb. 26, 1987, abandoned.

[51] Int. Cl.$^4$ .................. A61K 31/38; A61K 31/34; C07D 333/12; C07D 307/02
[52] U.S. Cl. .................. 514/438; 514/445; 514/448; 514/471; 549/62; 549/64; 549/65; 549/71; 549/74; 549/475; 549/476; 549/478; 549/484; 549/485; 549/486; 549/491
[58] Field of Search .............. 549/62, 64, 65, 71, 549/74, 475, 476, 478, 484, 485, 486, 491; 514/438, 445, 448, 471

[56] References Cited

U.S. PATENT DOCUMENTS 3,211,741  10/1965  Martin et al. .................. 549/74
4,128,561  12/1978  Braye .................. 549/74

FOREIGN PATENT DOCUMENTS 0055471  7/1982  European Pat. Off. .......... 514/438

OTHER PUBLICATIONS

Padgett, S. R., Wimalasena, K., Herman, H. H. Sirimanne, S. R., and May, S. W., Biochemistry, 24, 5826–5839, 1985.

Colombo, G. and Villafranca, J., *J. Biol. Chem.* 259(24), 15017–15020, 1984.

*Primary Examiner*—Alan Siegel

[57] ABSTRACT

This invention relates to novel heterocyclyl-2-propyn-1-amines which are useful as dopamine beta hydroxylase inhibitors in the treatment of hypertension.

18 Claims, No Drawings

HETEROCYCLYL-2-PROPYN-1-AMINES

CROSS-REFERENCE TO RELATED APPLICATION

This is a continuation of application Ser. No. 019,103, filed Feb. 26, 1987, now abandoned.

This invention relates to novel heterocyclyl-2-propyn-1-amines, to intermediates and processes for their production and to pharmaceutical compositions and methods of treating hypertension with such compounds.

More specifically, this invention relates to propynyl amines of the general formula

  (I)

wherein Het is 2- or 3-thienyl or 2- or 3-furyl, each of the Het thienyl and furyl rings optionally being substituted with from 1 to 3 moieties selected from the group consisting of lower alkyl of from 1 to about 6 carbon atoms, alkoxy of from 1 to about 6 carbon atoms, alkylthio of from 1 to about 6 carbon atoms, carboxylic acid, halo or hydroxymethyl and the therapeutically acceptable acid addition salts thereof. The compounds are inhibitors of dopamine beta hydroxylase, and are useful as antihypertensive agents.

When thienyl or furyl heterocyclic rings are di- or trisubstituted, and substituents can be the same or they can be different. Preferably, the heterocycle is either unsubstituted or is monosubstituted.

As used herein, the term "lower alkyl" means and includes groups from one to about six carbon atoms and include methyl, ethyl, propyl, butyl, pentyl and hexyl groups, which can be straight- or branched-chain groups. The term "alkoxy" refers to —OR groups wherein R is defined as lower alkyl above. The term "alkylthio" refers to —SR groups wherein R is defined as lower alkyl above. The term "halo" refers to chloro, bromo and fluoro. The preferred substituents include methyl; methoxy; methylthio and halo.

Illustrative examples of compounds of this invention include 3-(2-thienyl)-2-propyn-1-amine; 3-(3-thienyl)-2-propyn-1-amine; 3-(2-furyl)-2-propyn-1-amine; 3-(3-furyl)-2-propyn-1-amine; 3-[2-(5-chlorothienyl)]-2-propyn-1-amine; 3-[2-(5-methylthienyl)]-2-propyn-1-amine; 3-[2-(5-fluorothienyl)]-2-propyn-1-amine; 3-[3-(5-methylthiothienyl)]-2-propyn-1-amine; 3-[3-(5-hydromethylthienyl)]-2-propyn-1-amine; 3-[2-(5-methylfuryl)]-2-propyn-1-amine; 3-[3-(5-fluorofuryl)]-2-propyn-1-amine; 3-[3-(5-carboxyfuryl)]-2-propyn-1-amine and the therapeutically acceptable acid addition salts thereof.

Representative salts are those salts formed with non-toxic organic or inorganic acids, such as, for example, those formed from the following acids: hydrochloric, hydrobromic, sulfonic, sulfuric, phosphoric, nitric, maleic, fumaric, benzoic, ascorbic, succinic, methanesulfonic, acetic, propionic, tartiaric, citric, lactic, malic, mandelic, cinnamic, palmitic, itaconic, benzenesulfonic and toluenesulfonic.

The propynylamines (I) of this invention can readily be prepared by a series of reactions illustrated by the following reaction scheme:

(II)  (III)

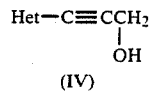

(IV)

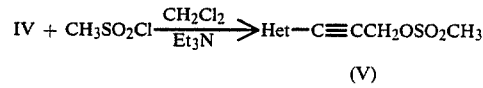

(V)

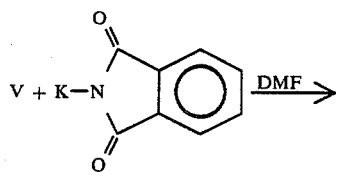

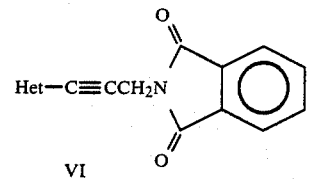

(VI)

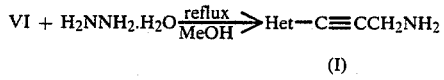

(I)

wherein $\phi$ represents phenyl, and Het is as previously defined.

In essence, the foregoing reaction scheme shows that the propynylamines of group (I) can be prepared by reacting the appropriate 2-propyn-1-yl phthalimide (VI) with hydrazine hydrate ($H_2NNH_2.H_2O$) in an organic solvent such as methanol (MeOH) under reflux conditions. The appropriate phthalimide (VI) can be obtained by known methodology, one route of which is presented in the reaction scheme above, wherein 2-propyn-1-ol (III) is reacted with an appropriate 2- or 3-iodide-substituted heterocycle (II) wherein Het is as described above, in the presence of catalysts such as bis(triphenylphosphine)palladium (II) chloride [$(\phi_3P)_2PdCl_2$] and copper iodide (CuI), and triethylamine ($EtN_3$) under nitrogen to produce the alcohols depicted by (IV). The appropriate alcohol can then be combined with methanesulfonyl chloride ($CH_3SO_2Cl$) in the presence of dichloromethane ($CH_2Cl_2$) and $Et_3N$ to form the appropriate mesylate (V) and the mesylate can then be reacted with potassium phthalimide (K-phthalimide) in N,N-dimethylformamide (DMF) to produce (VI). The free bases of the compounds in group (I) can be converted to acid addition salts by conventional methodology.

The foregoing reaction scheme is further illustrated by the following specific example:

EXAMPLE 1

3-(2-thienyl)-2-propyn-1-amine

A mixture of CuI (5.96 grams (g); 0.0313 moles (m)), bis(triphenylphosphine)palladium chloride (11.0 g; 0.0157 m) and 800 ml triethylamine was added via syringe to a solution (under nitrogen) of 2-propyn-1-ol (27.2 g; 0.485 mole) in 50 ml triethylamine. To the resulting brown suspension was added a solution of 2-iodothiophene (84.9 g 0.404 mole) in 50 ml triethylamine. The solution was added thereto slowly via syringe. The reaction mixture was allowed to reach 40° C. before being cooled in an ice bath to 20° C. After 30 min., the mixture was filtered and the filtrate was concentrated at reduced pressure to yield a dark oil. Purification by bulb-to-bulb distillation (120° C./0.4 torr) yielded 49.6 g (89%) of the alcohol as yellow oil.

The alcohol (10.0 g, 0.0725 mole) was mixed with triethylamine (8.07 g 0.0797 mole) and the resulting mixture was added dropwise to a solution of 9.1 g (0.0794 mole) methanesulfonyl chloride in 100 ml of dichloromethane at 0° C. under nitrogen ($N_2$). The temperature during the addition was kept below 15° C. After 15 min. from the completion of the first addition, an additional 2.0 ml of methanesulfonyl chloride were added to the mixture. After 10 min., the reaction mixture was partitioned between dichloromethane and 1N HCl. The dichloromethane layer was washed with saturated $NaHCO_3$ solution, dried over $K_2CO_3$, and concentrated at 25° C. in vacuo to give the unstable oily mesylate.

The crude mesylate thus obtained was immediately taken up in 200 ml DMF, potassium phthalimide (14.44 g, (0.078 mole) was added, and the mixture was stirred at 25°–30° C. for 45 min. Completion of the reaction was judged by tracking the presence of starting material by tlc (20% ethylacetate/hexane). The reaction mixture was partitioned between water and dichloromethane, and the dichloromethane layer was dried over $K_2CO_3$ and concentrated to a brown semi-solid. This material was dissolved in ether, washed with water, decolorized again with carbon, dried over $K_2CO_3$, and filtered and concentrated. The resulting pale yellow solid was recrystallized from hexane/ethyl acetate to provide a total of 3.89 g (20%) phthalimide.

The phthalimide (3.72 g, 13.9 mmol) was suspended in 40 ml methanol, hydrazine hydrate (0.76 ml, 15.7 mmol) was added, and the mixture was warmed to reflux. The reaction was judged complete by tlc monitoring (25% hexane/chloroform), the cooled mixture was partitioned between 1N KOH and ether. The ether layer was washed with saturated NaCl solution, dried over $K_2CO_3$, and concentrated to a pale yellow oil which was purified by bulb-to-bulb distillation (160° C./1.0 torr) yielding 1.46 g (76%) free base. 'H-nmr (60 MHz, $CDCl_3$) 6.8–7.3 (complex pattern, 3H, thienyl protons), 3.59 (S, 2H, $CH_2$), 1.40 (S, 2H, $NH_2$). The free base was taken up in ether and treated with ethereal HCL to precipitate the hydrochloride. The ether was removed in vacuo at 25° C. and the residue was recrystallized from 2-propanol, providing 1.82 g of the desired title product as colorless crystals with a mp of 199°–200° C. Anal Calcd for $C_7H_7NS.HCl$: C, 48.41; H, 4.64; N, 8.07; Found: C, 48.37; H, 4.53; N, 8.14.

The compounds of this invention exert in vitro and in vivo pharmacological effects as they inhibit dopamine-beta-hydroxylase (DBH) and, as such, are useful in the treatment of hypertension. As embodiment of this invention thus includes a method of treating hypertension in a mammal in need thereof which comprises administering internally to said animal an effective antihypertensive amount of a compound of formula I. Since DBH is a major enzyme in the synthetic pathway of norepinephrine (NE), it would be expected that the presence of an inhibitor would act to decrease the amount of NE produced, and thereby have an antihypertensive effect.

The DBH inhibitory properties of the compounds of this invention can readily be determined by standard and well-known procedures. For instance, determination of whether DBH inhibition demonstrates time-dependent kinetics is exemplified by a procedure wherein enzymatic oxygenation by DBH is determined in aqueous solution in the presence of molecular oxygen, an electron donor such as ascorbate, and the necessary cofactors for the enzyme at a pH of 4.5 to 5.5, preferably pH 5.0, and at a temperature of 20° C. to 40° C., preferably 37° C. The test compound is added at the desired concentration, and the system is incubated. At different time internals, aliquots are taken and DBH activity is measured using tyramine as the substrate. The reaction is followed by measuring oxygen uptake using a polarographic electrode and an oxygen monitor by the method of S. May et al., *J. Bio. Chem.* 256, 2258 (1981). In tests utilizing the above described procedure, the DBH inhibitory activity of the test compound increased as a function of the time of incubation, as indicated in Table I.

TABLE I

TIME-DEPENDENT
DBH INHIBITORY ACTIVITY - IN VITRO

| Compound | Concentration (M) | t ½ |
|---|---|---|
| 3-(2-thienyl)-2-propyn-1-amine | $5 \times 10^{-5}$ | 9.2 min. | t ½: time required for 50% log activity remaining

The ability of the compounds of this invention to lower blood pressure can be determined in vivo using standard and well-known procedures such as those employed for the continuous recording of arterial blood pressure in conscious animals. For instance, test compounds are administered intraperitoneally (ip) to un-anesthetized spontaneously hypertensive rats and the arterial blood pressure is monitored continuously. In tests utilizing the above procedure, the antihypertensive effect of the test compound is readily apparent as indicated by the degree of lowering of mean blood pressure (MBP) noted in Table II.

TABLE II

DBH INHIBITORY ACTIVITY - IN VIVO

| Compound | Dose mg/kg | Max Change MBP +/St. dev. | Duration hours |
|---|---|---|---|
| 3-(2-thienyl)-2-propyn-1-amine | 30 (ip) | −20+/−8 mm Hg | 14 |

Thus, based upon these and other standard laboratory techniques used to evaluate DBH inhibitors by standard toxicity tests and by standard pharmacological assays for the determination of antihypertensive activity in mammals, and by comparison of these results with the results of known antihypertensive agents, the effective antihypertensive dosage of the compounds of this invention can readily be determined. In general, effective antihypertensive results can be achieved at a dose of about 5 to about 100 mg per kilogram body weight per day. Of course, the specific initial and continuing dosage regimen for each patient will vary according to the nature and severity of the hypertension as determined by the attending diagnostician.

In their function as therapeutically useful compounds, it is advantageous to administer antihypertensive amounts of the compounds of this invention to the host animal as compositions in admixture with a pharmaceutical carrier suitable for enteral or parenteral administration. Such compositions may be in such forms as, for example, tablets, capsules and suppositories, or in liquid forms, as for example, elixirs, emulsions, sprays and injectables. In the formulation of pharmaceutical compositions, one skilled in the art can readily select those substances which do not react with the compounds of this invention, such as, for example, water, gelatin, lactose, starches, magnesium stearate, talc, vegetable oils, benzyl alcohols, gums, polyalkylene glycols, petroleum jelly and the like. The active ingredient is preferably present in the composition in such proportions by weight that the proportion by weight of the active ingredient to be administered lies between 0.1% and 50%.

What is claimed is:

1. A compound of the formula

$$\text{Het-C} \equiv \text{C-CH}_2\text{-NH}_2$$

wherein Het is 2- or 3-thienyl or 2- or 3-furyl, each Het ring optionally being substituted with from 1 to 3 moieties selected from the group consisting of lower alkyl of from one to about six carbon atoms, alkoxy of from 1 to about 6 carbon atoms, alkylthio of from 1 to about 6 carbon atoms, fluoro, bromo, chloro, carboxylic acid and hydroxymethyl and the pharmaceutically acceptable acid addition salts thereof.

2. A compound of claim 1 wherein Het is 2- or 3-thienyl.

3. A compound of claim 1 wherein Het is 2- or 3-furyl.

4. A compound of claim 2 which is 3-(2-thienyl)-2-propyn-1-amine.

5. A compound of claim 2 wherein Het is 3-thienyl.

6. A compound of claim 3 wherein Het is 2-furyl.

7. A compound of claim 3 wherein Het is 3-furyl.

8. A compound of claim 1 wherein Het is substituted 2- or 3-thienyl.

9. A compound of claim 8 wherein Het is monosubstituted with chloro, bromo, fluoro, methyl or methylthio.

10. A compound of claim 9 wherein the substitution is at the 5 position of the Het ring.

11. A compound of claim 10 wherein the monosubstitution is chloro, fluoro or bromo.

12. A compound of claim 1 wherein Het is substituted 2- or 3-furyl.

13. A compound of claim 12 wherein Het is monosubstituted with chloro, bromo, fluoro, methyl or methylthio.

14. A compound of claim 12 wherein the monosubstitution is as the 5 position of the Het ring.

15. A compound of claim 13 wherein the monosubstitution is chloro, fluoro or bromo.

16. A composition comprising a compound of formula I and a pharmaceutically acceptable carrier.

17. A method of treating hypertension in a mammal which comprises administering internally to a mammal an effective amount of a compound of formula I.

18. The method of claim 17 wherein the compound is 3-(2-thienyl)-2-propyn-1-amine.

* * * * *